(12) United States Patent
Ruan et al.

(10) Patent No.: US 10,220,160 B2
(45) Date of Patent: Mar. 5, 2019

(54) PEN NEEDLE ASSEMBLY FOR PREVENTING UNDER-TORQUING AND OVER-TORQUING OF PEN NEEDLE

(71) Applicant: Becton, Dickinson and Company, Franklin Lakes, NJ (US)

(72) Inventors: Tieming Ruan, Randolph, NJ (US); Abhijitsinh S. Raj, Parsippany, NJ (US); Joshua D. Horvath, Sparta, NJ (US); Adam Gold, New York, NY (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 447 days.

(21) Appl. No.: 14/973,404

(22) Filed: Dec. 17, 2015

(65) Prior Publication Data
US 2016/0101241 A1 Apr. 14, 2016

Related U.S. Application Data

(63) Continuation of application No. 14/162,416, filed on Jan. 23, 2014, now Pat. No. 9,233,216, which is a
(Continued)

(51) Int. Cl.
*A61M 5/00* (2006.01)
*A61M 5/34* (2006.01)
(Continued)

(52) U.S. Cl.
CPC .......... *A61M 5/343* (2013.01); *A61M 5/3202* (2013.01); *A61M 5/3213* (2013.01);
(Continued)

(58) Field of Classification Search
CPC .. A61M 5/3202; A61M 5/347; A61M 5/3213; A61M 2005/3254; A61M 5/002;
(Continued)

(56) References Cited

U.S. PATENT DOCUMENTS

| 2,983,503 A | 5/1961 | Haussermann |
| 3,507,279 A * | 4/1970 | Senkowski ........... A61M 5/347 604/241 |

(Continued)

FOREIGN PATENT DOCUMENTS

| CA | 2618587 | 7/2008 |
| EP | 0903156 | 3/1999 |

(Continued)

OTHER PUBLICATIONS

Canadian Office Action, dated Sep. 18, 2014, in related CA Application No. 2,639,320.

*Primary Examiner* — Kevin C Sirmons
*Assistant Examiner* — William R Carpenter
(74) *Attorney, Agent, or Firm* — Dickinson Wright PLLC

(57) ABSTRACT

A pen needle hub and cover for a pen needle assembly that provides tactile and/or audible indicia of proper attachment between the hub of the pen needle and the pen is provided. Such indicia substantially prevent under- and over-torquing of the pen needle. The tactile indicia may include a user sensing a wave of a torque of peak value followed by a torque of lesser value.

5 Claims, 13 Drawing Sheets

Related U.S. Application Data continuation of application No. 12/205,717, filed on Sep. 5, 2008, now Pat. No. 8,672,902.

(60) Provisional application No. 60/935,955, filed on Sep. 7, 2007.

(51) Int. Cl.
  *A61M 5/32* (2006.01)
  *A61M 5/50* (2006.01)
  *A61M 5/24* (2006.01)

(52) U.S. Cl.
  CPC .......... *A61M 5/3293* (2013.01); *A61M 5/347* (2013.01); *A61M 5/5086* (2013.01); *A61M 5/24* (2013.01); *A61M 2005/3254* (2013.01); *A61M 2205/581* (2013.01); *A61M 2205/582* (2013.01)

(58) Field of Classification Search
  CPC .................. A61M 5/3293; A61M 5/24; A61M 2005/3206; A61M 2039/1033; A61M 2039/1044; A61M 2005/3118; A61M 2205/581; A61M 5/158; A61M 5/34
  See application file for complete search history.

(56) References Cited

U.S. PATENT DOCUMENTS

| | | | |
|---|---|---|---|
| 3,967,621 A * | 7/1976 | Schwarz | A61M 5/288 604/192 |
| 4,740,205 A | 4/1988 | Seltzer | |
| 5,117,837 A | 6/1992 | Wanamaker et al. | |
| 5,163,907 A * | 11/1992 | Szuszkiewicz | A61M 5/322 604/110 |
| 5,360,404 A | 11/1994 | Novacek | |
| 5,591,143 A | 1/1997 | Trombley | |
| 5,611,786 A | 3/1997 | Kirchhofer | |
| 5,873,462 A | 2/1999 | Nguyen | |
| 5,931,817 A | 8/1999 | Nguyen | |
| 5,941,857 A | 8/1999 | Nguyen | |
| 5,968,021 A | 10/1999 | Ejlersen | |
| 5,971,966 A | 10/1999 | Lav | |
| 6,152,913 A | 11/2000 | Feith | |
| 6,346,094 B2 | 2/2002 | West | |
| 6,840,291 B2 * | 1/2005 | Caizza | A61M 5/3234 141/18 |
| 6,991,608 B2 | 1/2006 | Young | |
| 7,134,550 B2 | 11/2006 | Groth | |
| 7,247,153 B2 | 7/2007 | Guala | |
| 7,384,414 B1 * | 6/2008 | Marshall | A61M 5/326 604/198 |
| 7,665,605 B2 | 2/2010 | Erickson | |
| 8,057,444 B2 | 11/2011 | Hartmann | |
| D665,497 S | 8/2012 | Marshall | |
| 2003/0187409 A1 | 10/2003 | Erickson | |
| 2004/0153038 A1 | 8/2004 | Guala | |
| 2004/0199085 A1 | 10/2004 | Young et al. | |
| 2005/0273076 A1 | 12/2005 | Beasley | |
| 2006/0032769 A1 * | 2/2006 | Erickson | A61M 5/002 206/365 |
| 2006/0229562 A1 | 10/2006 | Marsh | |
| 2007/0149924 A1 | 6/2007 | Marsh | |
| 2008/0154192 A1 | 6/2008 | Schraga | |
| 2008/0275429 A1 * | 11/2008 | Sage | A61M 25/0014 604/536 |
| 2009/0118678 A1 | 5/2009 | Kawashima | |
| 2009/0143746 A1 | 6/2009 | Mudd et al. | |
| 2012/0071835 A1 | 3/2012 | Marshall | |
| 2012/0277685 A1 | 11/2012 | Limaye | |

FOREIGN PATENT DOCUMENTS

| | | |
|---|---|---|
| EP | 1384491 | 1/2004 |
| EP | 1949927 | 7/2008 |
| JP | 06-190041 | 7/1994 |
| JP | 10-113585 | 5/1998 |
| JP | 2004-305749 | 11/2004 |
| JP | 2004-321826 | 11/2004 |
| JP | 2004-329923 | 11/2004 |
| JP | 3114468 | 8/2005 |
| JP | 2006-224981 | 8/2006 |
| JP | 2007-098109 | 4/2007 |
| WO | 2008/028305 | 3/2008 |

* cited by examiner

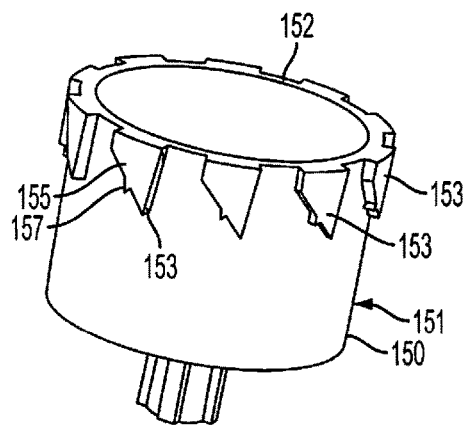 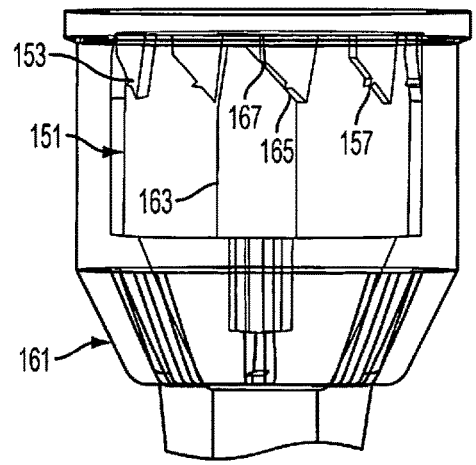
FIG. 5          FIG. 6
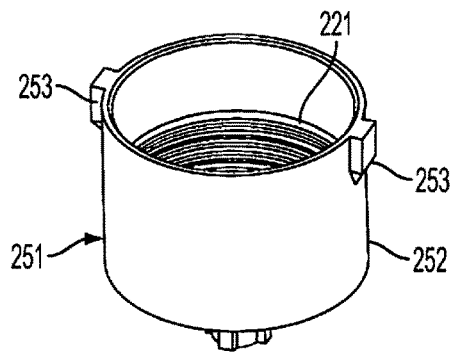
FIG. 7
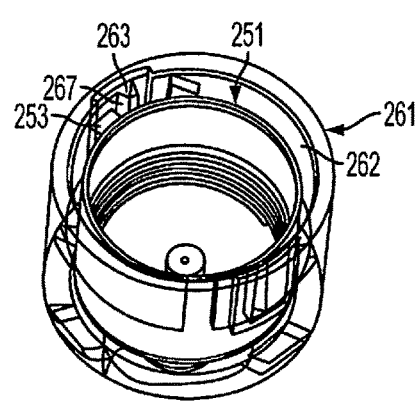 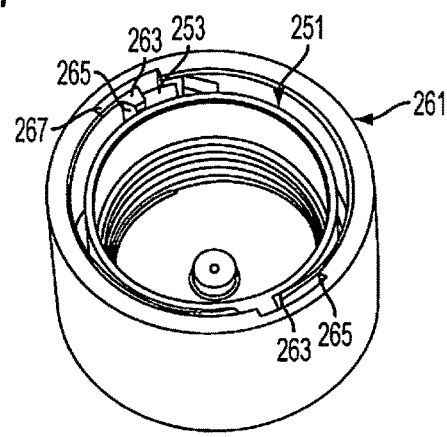
FIG. 8          FIG. 9

PEN NEEDLE ASSEMBLY FOR PREVENTING UNDER-TORQUING AND OVER-TORQUING OF PEN NEEDLE

CROSS REFERENCE TO RELATED APPLICATION

This application is a divisional application under 35 U.S.C. § 120 of U.S. Ser. No. 14/162,416, filed Jan. 23, 20145 which is a continuation of U.S. patent application Ser. No. 12/205,717, filed Sep. 5, 2008, which claims the benefit under 35 U.S.C. § 119(e) of provisional application Ser. No. 60/935,955, filed Sep. 7, 2007, all of said prior applications being incorporated herein in their entirety.

FIELD OF THE INVENTION

The present invention relates generally to a pen needle assembly that substantially prevents under- and over-torquing of the pen needle. More particularly, the present invention generally relates to a pen needle that provides audible and/or tactile indicia that the pen needle is properly attached to the corresponding pen injector, thereby substantially preventing under- and over-torquing of the pen needle. Still more particularly, the present invention generally relates to providing tactile indicia in which a torque of peak value is followed by a torque of lower value, thereby indicating proper attachment of the pen needle to the corresponding pen indicator.

BACKGROUND OF THE INVENTION

Insulin and other injectable medications are commonly given with drug delivery pens, whereby a disposable pen needle is attached to facilitate drug container access and allow fluid egress from the container through the needle into the patient.

As technology and competition advance, driving the desire for shorter, thinner, less painful, and more efficacious injections, the design of the pen needle and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

Drug delivery pens, such as the existing drug delivery pen 100 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the lead screw 7 and stopper 15 through the medicament cartridge 12 attached through the reservoir housing or hub 20. In standard drug delivery pens the dosing and delivery mechanisms are all found within the outer sleeve 13 and are not described in greater detail here as they are understood by those knowledgeable of the prior art. The medicament cartridge 12 is typically attached to a standard pen injector housing via known attachment means, such as ¼ turn fastening features.

The distal movement of the plunger or stopper 15 within the medicament cartridge 12 causes medication to be forced into the reservoir housing 20. The medicament cartridge 12 is sealed by septum 16, which is punctured by a septum penetrating needle cannula (not shown) located within reservoir housing 20. Reservoir housing 20 is preferably screwed onto the medicament cartridge 12, although other attachment means can be used. To protect the patient needle 11, an outer shield 69 attaches to the pen needle assembly 9. An inner shield 59 covers the patient needle 11 within the outer shield 69. The cap 21 fits snugly against outer sleeve 13 to allow a user to securely carry the drug delivery pen 100.

Another existing pen needle assembly 2 is shown in FIG. 3. The needle assembly 2 includes a cover 101, an inner shield 200, a needle cannula 300, and a needle hub 400. A proximal end 310 of the needle cannula 300 is inserted into a center opening in the distal (patient) end 405 of the needle hub 400 until a predetermined length of the distal end 305 of the needle cannula 300 remains extended. The needle cannula 300 is secured by epoxy or adhesive in the distal end 405 of the hub 400 within the hub protrusion 420.

To protect users from injury and the needle cannula 300 from being damaged, the inner shield 200 covers the exposed portion of needle cannula 300. The open proximal end 210 of the inner shield 200 is placed over the exposed portion of needle cannula 300. The open proximal end 110 of the cover 100 envelops the inner shield 200, needle cannula 300, and hub 400.

Distal end 105 of the cover 101 is closed to prevent contamination and damage to the inner components of pen needle assembly 2, and to prevent injury to anyone who may handle it prior to use. The proximal end 410 of the hub 400 is typically covered by a sanitary cover (not shown) on end 110 of cover 101. The pen needle assembly 2 is then ready for shipment to a user. When the user is ready to use the pen needle assembly 2, the sanitary cover (not shown) is removed, the hub 400 is screwed onto a standard medication cartridge 12 (FIG. 2), and the cover 101 and inner shield 200 are separately removed from the hub 400/cannula 300 subassembly by a pulling action. The distal end 205 of the inner shield 200 is closed to cover the distal end 305 of the needle cannula 300 after the cover 101 is removed to protect the user from an accidental stick. The inner shield 200 is then removed to access the needle cannula 300. Thus, two separate pulling actions are required to remove both the cover 101 and the inner shield 200.

FIG. 4 is a cross-sectional view of a pen needle assembly 2 in the configuration that it would be received by a user (with a sanitary cover not shown). An inner shield 470 covers a needle cannula 430. Additionally, the hub 460 includes a center hub protrusion 465. The skin contact plane 450 is the plane of the straight surface across the distal end of the center hub protrusion 465.

As noted above, the needle hub 400 is threadably engaged with a standard pen or medication cartridge 12 (FIGS. 1 and 2). However, these existing pen hubs do not provide positive confirmation that the pen needle is appropriately connected to the pen. This often results in the user under- or over-torquing the pen needle, thereby resulting in an inaccurate dosage and other associated problems.

Pen needle assemblies are also disclosed in U.S. Patent Application Publication Nos. 2006/0229562 to Marsh et al. and 2007/0149924 to R. Marsh, the entire contents of both of which are hereby incorporated by reference.

Accordingly, a need exists for a pen needle hub that positively confirms appropriate connection between the hub and the corresponding pen.

SUMMARY OF THE INVENTION

In accordance with an aspect of the present invention, a pen needle hub provides tactile and/or audible indicia that the hub is properly connected to a corresponding pen, thereby substantially preventing under- and over-torquing of the pen needle hub.

In accordance with another aspect of the present invention, audible indicia is created when a first member on the pen needle hub passes over a corresponding second member on a cover in which the pen needle hub is disposed, or when the second member on the cover passes over the first member on the hub.

In accordance with another aspect of the present invention, tactile indicia is created when a first member on the pen needle hub passes over a corresponding second member on a cover in which the pen needle hub is disposed, or when the second member on the cover passes over the first member on the hub.

In accordance with another aspect of the present invention, the tactile indicia includes a user sensing a wave of a torque of peak value followed by a torque of lesser value.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIG. 5 is a perspective view of a pen needle hub according to a first exemplary embodiment of the present invention;

FIG. 6 is an elevational view of the pen needle hub of FIG. 1 received by a cover according to a first exemplary embodiment of the present invention;

FIG. 7 is a perspective view of a pen needle hub according to a second exemplary embodiment of the present invention;

FIG. 8 is a perspective view of the hub disposed in a first position in a cover according to a second exemplary embodiment of the present invention;

FIG. 9 is a perspective view of the hub rotated to a second position in the cover;

Throughout the drawings, like reference numbers will be understood to refer to like parts, components and structures.

DETAILED DESCRIPTION OF THE EXEMPLARY EMBODIMENTS

Figure 1:
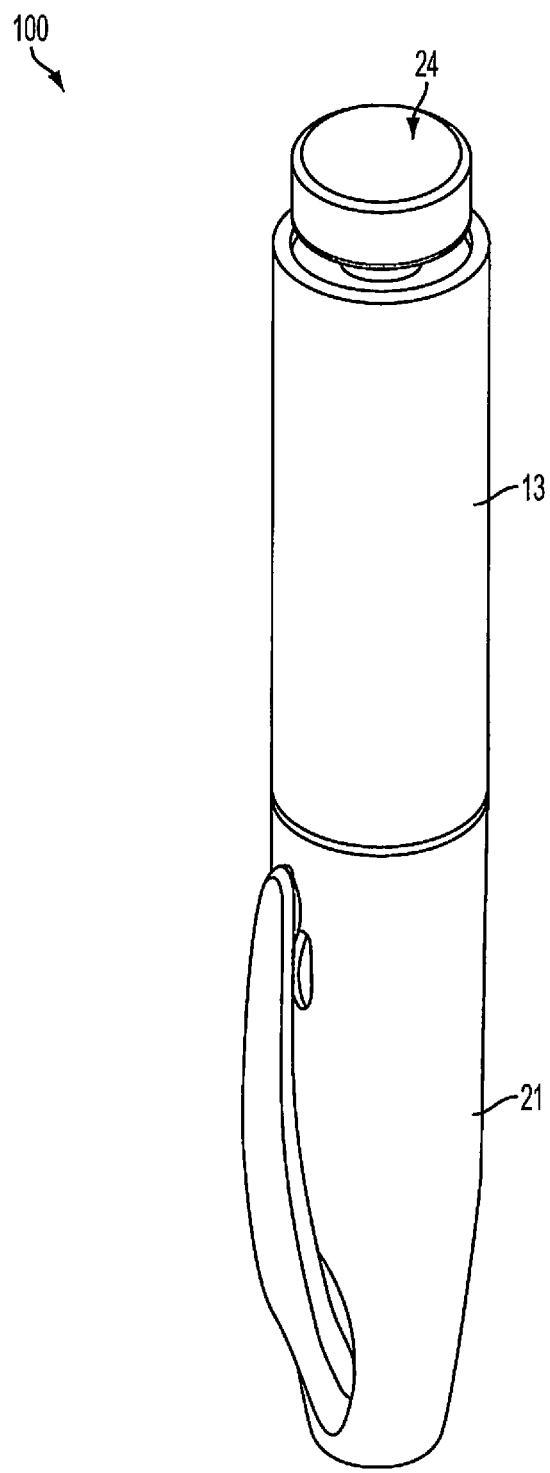
FIG. 1 is a perspective view of an assembled existing drug delivery pen.
Figure 2:
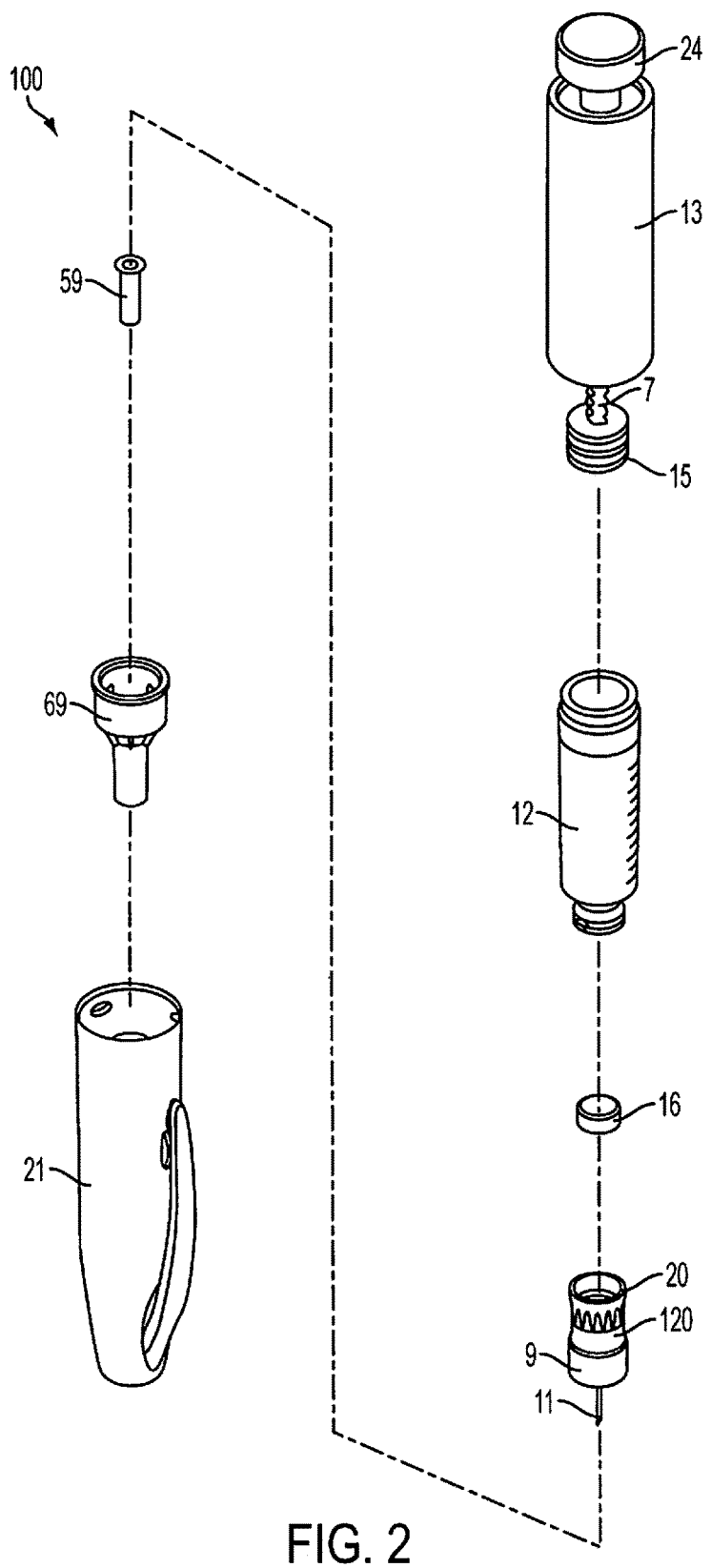
FIG. 2 is an exploded perspective view of the components of the drug delivery pen of FIG. 1.
Figure 3:
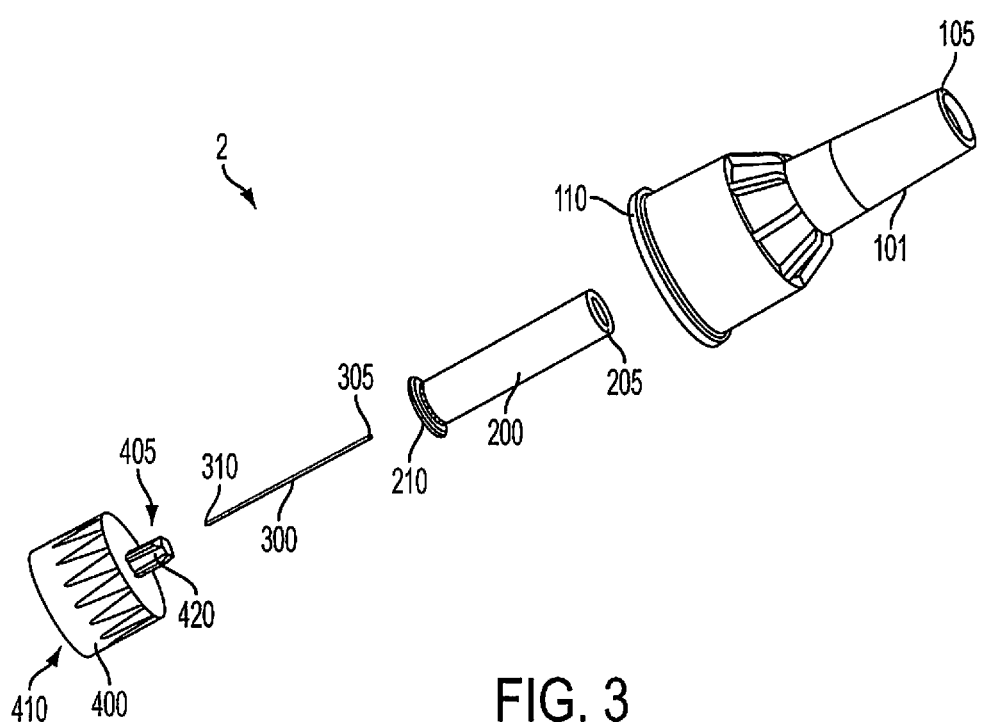
FIG. 3 is an exploded perspective view of a needle assembly for a drug delivery pen.
Figure 4:
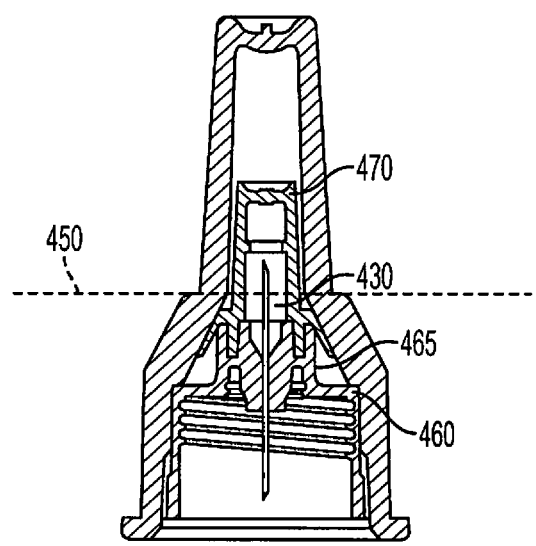
FIG. 4 is a cross-sectional view of the pen needle hub assembly of FIG. 3 in an as-manufactured state.

The following description and details of exemplary embodiments of the present invention, while generally disclosed in a typical drug delivery pen, as shown in FIGS. 1 and 2, could more broadly apply to a needle and hub assembly for use in conjunction with, or incorporated onto, other injection devices such as syringes and infusion devices.

In the exemplary embodiments of the present invention shown in FIGS. 5-32, a pen needle hub and cover assembly provide audible and/or tactile indicia that the pen needle hub is properly attached to the corresponding pen injector, thereby substantially preventing under- and over-torquing of the pen needle. The tactile indicia may include a user sensing a wave of a torque of peak value followed by a torque of lesser value. Features on a pen needle hub and a pen needle cover to generate audible/tactile indicia are exchangeable to suit this and different applications, and are preferably made of plastic. For example, the protruding part does not always need to be on the hub and the receiving part on the cover, but may be reversed or combined in any number of other suitable manners.

A first exemplary embodiment of the present invention is shown in FIGS. 5 and 6. The pen needle hub 151 has a plurality of protrusions 153 disposed on the outer surface 150 at the proximal end 152 of the hub, as shown in FIG. 5. When the hub 151 is disposed in a cover 161, a rib 163 on an inner surface of the cover is disposed between two adjacent protrusions 153 of the hub 151, as shown in FIG.

6. When a torque applied on the cover 161 is greater than a predetermined amount, the rib 163 slides on the slope 155 of a protrusion 153. A first tooth 157 is disposed on the slope 155 of the protrusion 153, and a second tooth 167 is disposed on a slope 165 of the rib 163.

Threads 221 (FIG. 7) disposed in the hub engage threads on the pen. The cover, which is connected to the hub in any suitable manner, is gripped by a user and rotated to threadably engage the pen needle with the pen. The torque required to threadably engage the hub with the pen is not sufficient to cause the cover 161 to rotate with respect to the hub 151. Once the hub 151 and pen are properly engaged, continued application of torque to the cover causes the cover to rotate with respect to the hub 151. The slope 165 of the rib 163 slides downwardly along the slope 155 of the protrusion 153. As the second tooth 167 passes over the first tooth 157, an audible indicia is generated indicating proper attachment between the hub 151 and pen. This movement of the cover 161 causes the cover to be pushed away from the proximal end 152 of the hub, until the rib 163 reaches the end of the protrusion 153, thereby moving into the space between the next two adjacent protrusions. Thus, tactile indicia are also generated to positively confirm appropriate attachment between a pen needle and a pen.

A second exemplary embodiment of the present invention is shown in FIGS. 7-17. A plurality of protrusions 253 are disposed on an outer surface 252 of a hub 251, as shown in FIGS. 7-9. A plurality of cantilever hooks 263 are disposed on an inner surface 262 of a cover 261, as shown in FIGS. 8 and 9. When the pen needle hub 251 is connected to the cover 261, there is an interface between the hub and the cover so that there is friction therebetween, thereby retaining the hub 251 within the cover 261. Preferably, the interface between the hub 251 and cover 261 is approximately 0.005 inches.

The cover 261 has a plurality of cuts with flexible cantilever hooks 263. When a torque applied on the cover is sufficient to overcome the frictional engagement between the hub 251 and cover 261, the protrusion 253 slides along the cantilever hook 263. When the protrusion 253 reaches a ramped surface 267 at an end of the cantilever hook 263, the protrusion snaps past the cantilever hook and into a cut 265 in the cover 251, thereby generating an audible indication that the hub and pen are appropriately connected.

Once the protrusion 253 is received in the cut 265 of the cover, there is no longer any friction between the hub 251 and the cover 261, such that the cover may be easily removed from the hub. The 265 cut substantially prevents further rotation of the cover 261. Alternatively, there may be a slight interference (preferably between approximately 0.002-0.003 inches, inclusive) between the hub 251 and the cover 261 such that cover retains the hub 251 after threadably disengaging the hub 251 from a pen injector.

Figure 10:
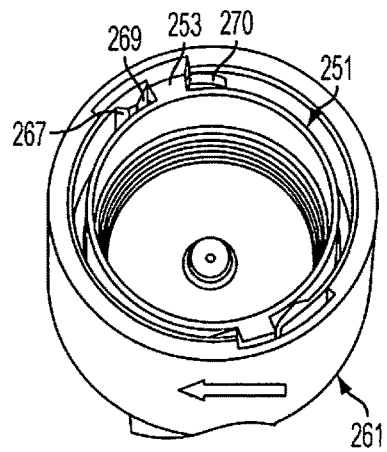
FIGS. 10-12 are perspective views of the hub rotating within the cover according to a second exemplary embodiment of the present invention.
Figure 11:
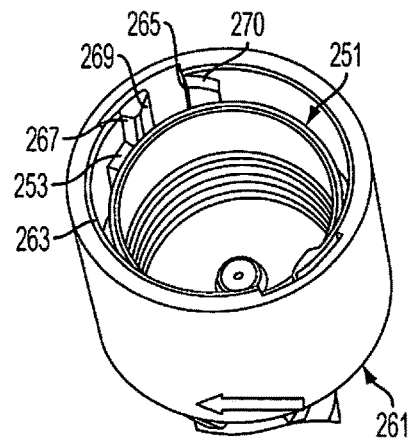
Figure 12:
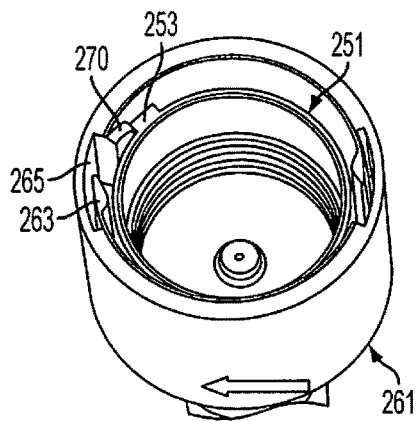
Figure 13:
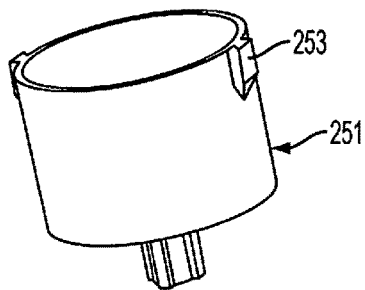
FIGS. 13-17 are perspective views of the pen needle hub and cover according to the second exemplary embodiment of the present invention.
Figure 14:
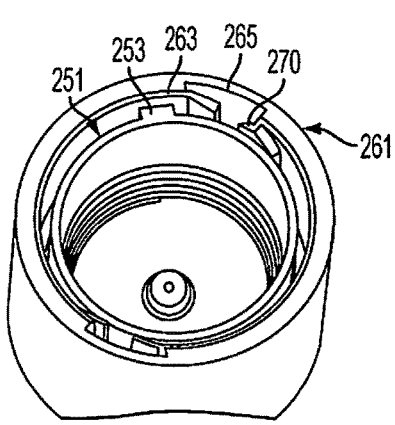

There may be a second ramp 269 on the cantilever hook 263 in addition to the first ramp 267, as shown in FIGS. 10-12. The first ramp 267 is steeper than the second ramp 269. For example, the first ramp has an angle of approximately 45 degrees, and the second ramp has an angle of approximately 30 degrees. Because of the locations and slopes of the first and second ramps, less torque ($T_2$) is required to overcome the second ramp 269 than is required to overcome the first ramp 267 ($T_1$).

When a pen needle is screwed onto a pen injector, the protrusions 253 of the hub 251 slide onto the first ramp 267 and generate a torque $T_1$. When a user puts the cover 261 back onto the pen needle hub 251, the projections 253 of the hub 251 are not in the cuts 265 on the cover 261. The torque applied on the cover 261 rotates the cover, thereby creating a firm contact between the protrusions 253 of the pen needle hub 251 and the tabs 270 of the cover 261, as shown in FIG. 12, thereby allowing the pen needle to be threadably disengaged from a pen injector.

When the protrusions 253 of the hub 251 are disposed in the cuts 265 of the cover 261, as shown in FIG. 10, the torque required to overcome the second ramp 269 ($T_2$) is less than the torque ($T_1$) required to overcome the first ramp 267. Thus, the protrusions 253 slide onto the second ramp 269 and contact an inner surface of the cover 261, as shown in FIG. 11. The torque applied on the cover 261 rotates the cover, thereby creating a firm contact between the protrusions 253 of the pen needle hub 251 and the tabs of the cover 261, as shown in FIG. 12. Thus, the pen needle may be threadably disengaged from the pen injector.

Figure 15:
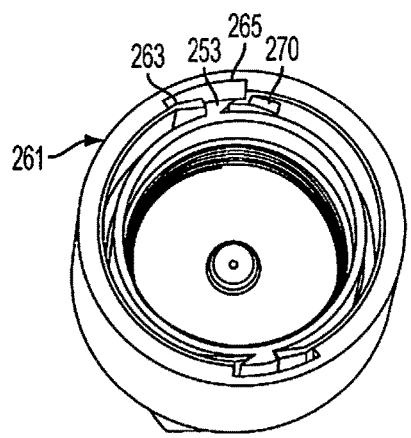
Figure 16:
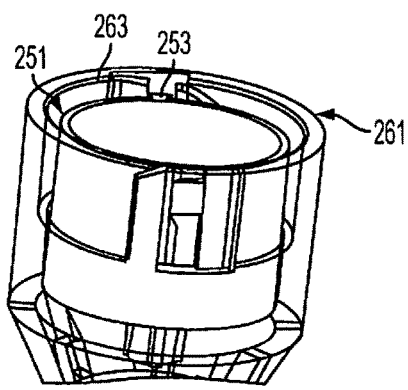
Figure 17:
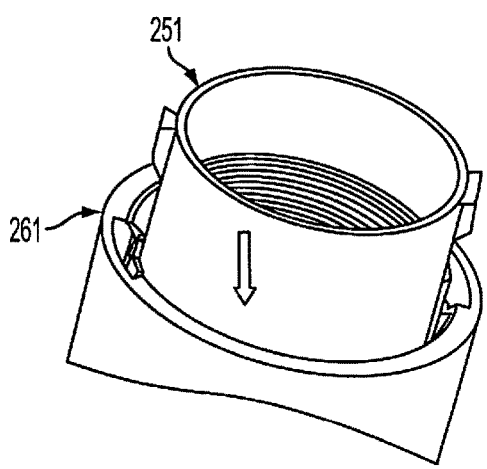

As shown in FIGS. 13-17, the protrusion 253 of the hub 251 bends the cantilever hook 253 instead of sitting inside of the cut 265 on the cover 261. As shown in FIGS. 15 and 16, the protrusion bends the cantilever hook 253 and is retained between the cantilever hook and the tab 270. Thus, the hub 251 does not fall out of the cover 261 when removing the hub from the pen injector.

Figure 18:
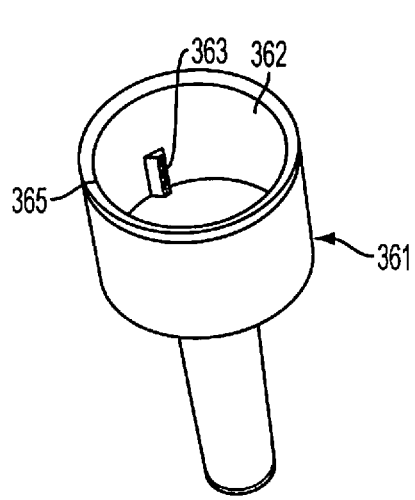
FIG. 18 is a perspective view of a pen needle hub according to a third exemplary embodiment of the present invention.
Figure 19:
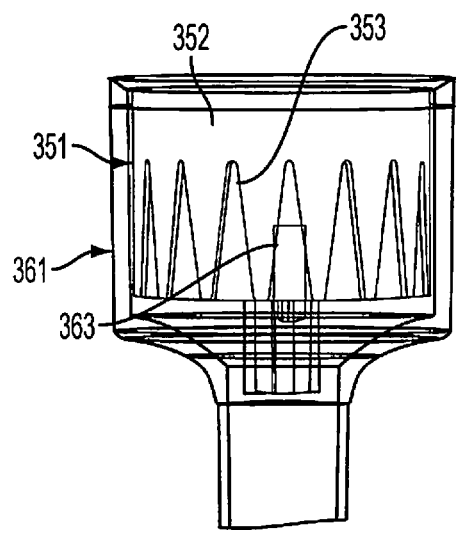
FIG. 19 is an elevational view of the pen needle hub of FIG. 18 disposed in a cover.

A third exemplary embodiment of the present invention is shown in FIGS. 18 and 19. A rib 363 having a ramped surface 365 is disposed on an inner surface 363 of the cover 361. When a pen needle hub 351 is disposed in a cover 361 and a torque applied on the cover is greater than a predetermined amount, the rib 363 passes over the substantially V-shaped grooves 353 on an outer surface 352 of the hub and generates a substantially continuous audible indicia. Preferably, the substantially V-shaped grooves are disposed around the entire circumference of the hub 351. Because of the profile of the rib 363, when a reverse torque is applied on the cover 361, the non-ramped surface of the rib prevents the rib from passing over the substantially V-shaped grooves 353 of the hub, thereby preventing the pen needle from being threadably disengaged from a pen. Additionally, because of the geometry of this embodiment, the cover 361 fits with any existing drug delivery pen caps. Even with the small sealing area without a flange, the cover 361 is still sealable using known heat sealing or other methods.

Figure 20:
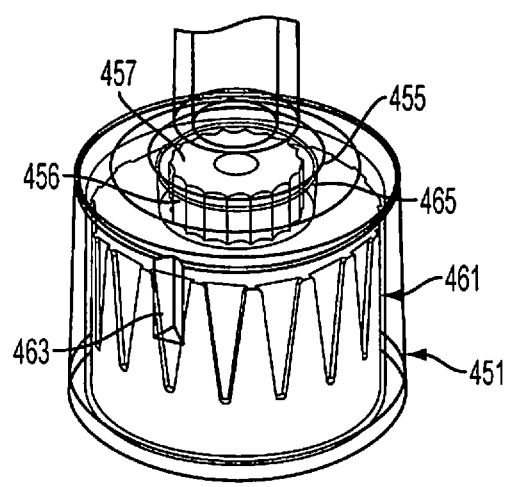
FIG. 20 is a perspective view of a pen needle hub disposed in a cover according to a fourth exemplary embodiment of the present invention.

A fourth exemplary embodiment of the present invention is shown in FIG. 20, which is substantially similar to the third exemplary embodiment shown in FIGS. 18 and 19. In addition to the V-shaped grooves 453 on the hub 451 and the corresponding rib 463 on the cover 461, a plurality of substantially circular cuts 455 are formed on an outer surface 456 of a central protrusion 457 of the hub 451. The cuts 455 are engaged by corresponding protrusions 465 formed on an inner surface of the cover 461. When the torque applied on the cover 461 is greater than a predetermined amount, the cover 461 slips on the hub 451 and generates audible indicia that the hub is properly connected to the pen injector.

Figure 21:
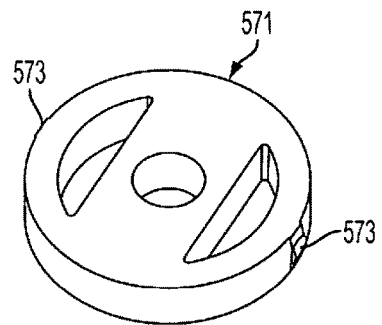
FIG. 21 is a perspective view of a ring according to a fifth exemplary embodiment of the present invention.
Figure 22:
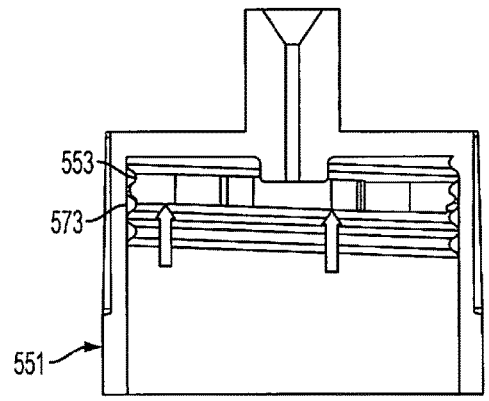
FIG. 22 is an elevational view of the ring of FIG. 21 disposed in a pen needle hub.

A fifth exemplary embodiment of the present invention is shown in FIGS. 21 and 22. A plastic ring 571 is initially disposed inside of a pen needle hub 551, as shown in FIG. 22. Two tabs 573 are disposed on each side of the plastic ring 571, and the tabs engage the threads 553 of the plastic hub 551. When a pen needle is threaded onto a pen, the ring 571 contacts the pen and is pushed along the threads, as indicated by the arrows in FIG. 22. Because the tabs 573 are flexible, audible indicia is generated as the tabs 573 pass over the hub threads 553 during the twisting on of a pen needle.

Figure 23:
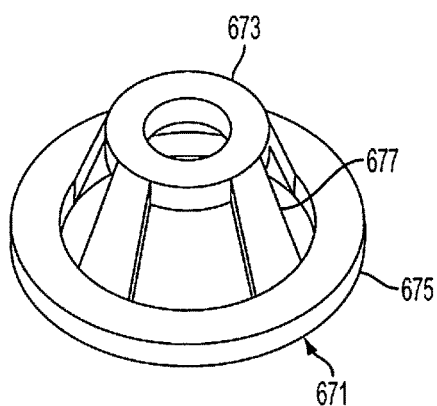
FIG. 23 is a perspective view of a ring according to a sixth exemplary embodiment of the present invention.
Figure 24A:
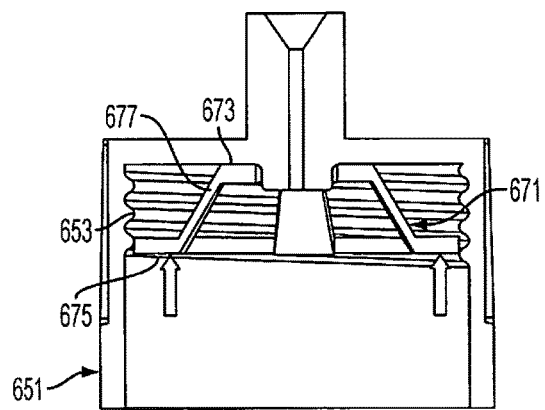
FIGS. 24A and 24B are elevational views of the ring of FIG. 23 disposed in a pen needle hub.
Figure 24B:
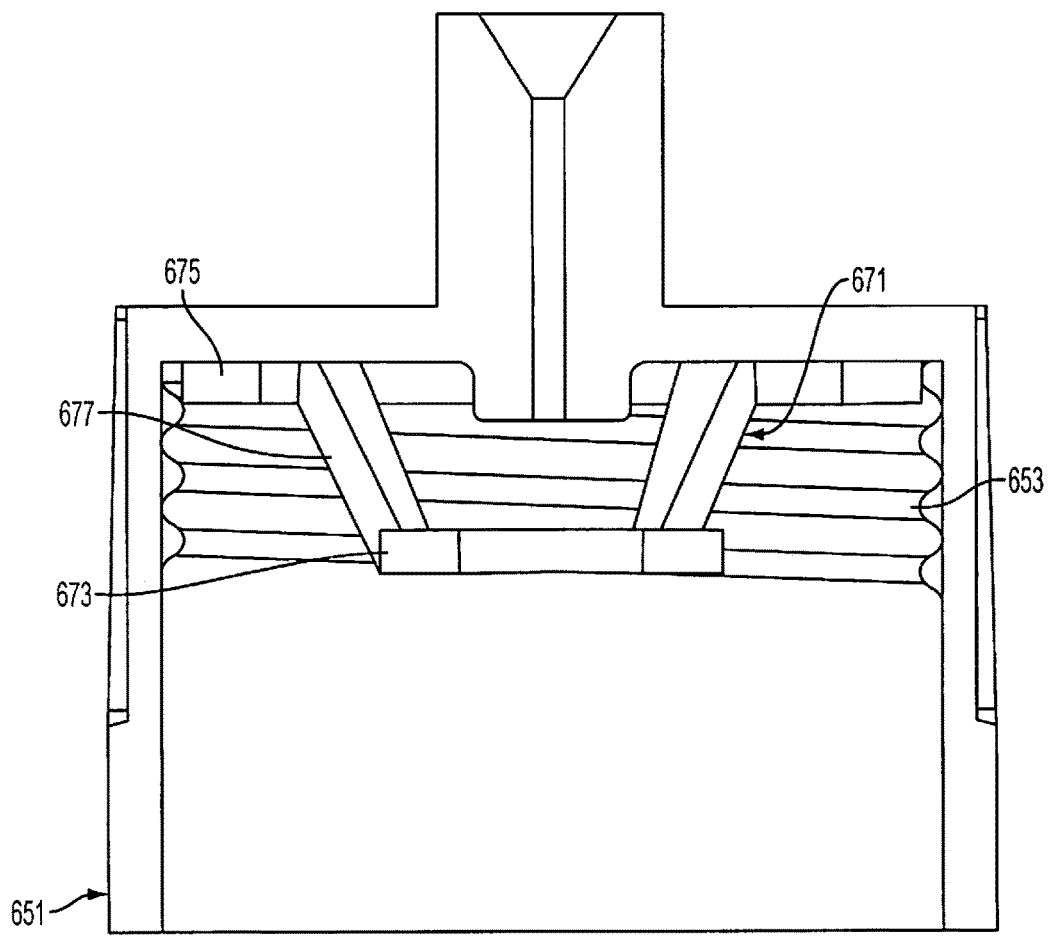

A sixth exemplary embodiment of the present invention is shown in FIGS. 23, 24A and 24B. A plastic dome 671 has an upper platform 673 connected to a lower platform 675 by a plurality of living hinges 677, as shown in FIG. 23. Threads 653 are also shown. The dome 671 is disposed inside of a pen needle hub 651. Interference between the dome 671 and the hub 651 retains the dome within the hub. When a pen needle is threadably engaged with a pen, the pen contacts the lower platform 675 of the plastic dome 671, thereby moving the lower platform upwardly toward the upper platform 673, as indicated by the arrows in FIG. 24A. The living hinges 677 allow the lower platform 675 to move with respect to the upper platform 673 and are compressed at the same time. As the lower platform 675 passes a certain point, the plastic dome 671 flips, and releases the energy stored inside of the living hinges. Audible indicia are generated to indicate proper attachment of the pen needle to the pen. The lower platform 675 contacts with the pen needle hub and the upper platform 673 contacts with the pen, as indicated in FIG. 24B.

Figure 25:
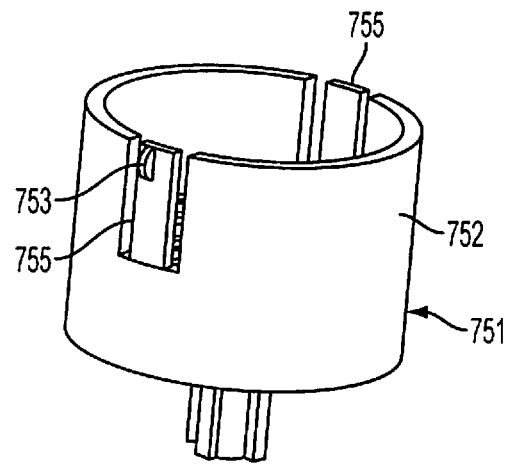
FIG. 25 is a perspective view of a pen needle hub according to a seventh exemplary embodiment of the present invention.
Figure 26:
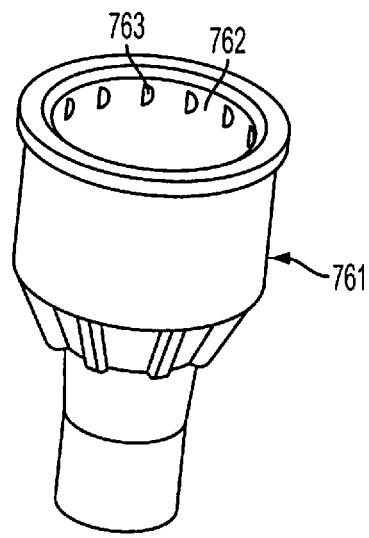
FIG. 26 is a perspective view of a cover according to a seventh exemplary embodiment of the present invention.
Figure 27:
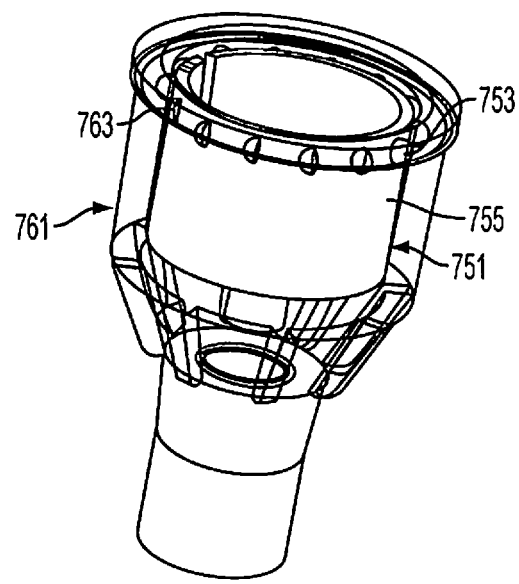
FIG. 27 is a perspective view of the hub of FIG. 25 disposed in the cover of FIG. 26.

A seventh exemplary embodiment of the present invention is shown in FIGS. 25-27. The needle hub 751 has two or more protrusions 753 extending outwardly from an outer surface 752 of the hub. Preferably, the protrusions 753 have a substantially half-hemispherical shape, as shown in FIG. 25. The cover 761 has a plurality of cavities disposed on the inner surface 762 thereof, as shown in FIG. 26. Preferably, the cavities are substantially equally spaced around the inner circumference of the cover 761. The hub 751 is then connected to the cover 761. When the torque applied on the cover is greater than a predetermined amount, the protrusions 753 of the hub 751 pass out of one cavity 763 and into the next cavity, as shown in FIG. 27. Thus, as the protrusions 753 pass from one cavity 763 to the next, audible indicia is generated indicating proper connection of the pen needle to the pen. Preferably, the protrusions 253 are formed on a flexible arm 755 connected to the hub 751, as shown in FIG. 25. The flexibility of the arm 755 facilitates movement of the protrusions 753 in and out of adjacent cavities 763 of the cover 761.

Figure 28:
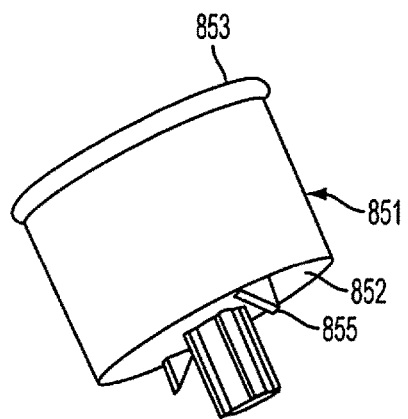
FIG. 28 is a perspective view of a pen needle hub according to an eighth exemplary embodiment of the present invention.
Figure 29:
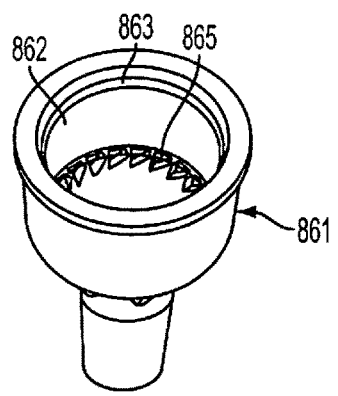
FIG. 29 is a perspective view of a cover according to an eighth exemplary embodiment of the present invention.
Figure 30:
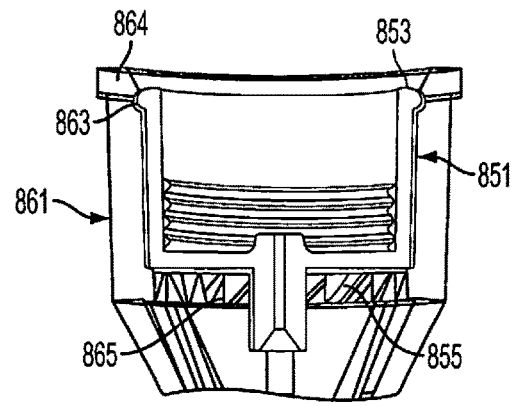
FIG. 30 is a perspective view of the hub of FIG. 28 disposed in the cover of FIG. 29.

An eighth exemplary embodiment of the present invention is shown in FIGS. 28-30. A pen needle hub 851 has a raised ring 853 disposed at a proximal end and a plurality of tabs 855 disposed on a distal surface 852, as shown in FIG. 28. A cover 861 has a circular cut 863 disposed in an inner surface 862 thereof, as shown in FIG. 29. A plurality of cavities 865 are also formed in the inner surface 862 of the cover 861. When initially attaching the hub 851 to the pen injector, the raised ring 853 is received within the cut 863 in the cover and the tabs 855 are received by the plurality of cavities 865, as shown in FIG. 30. Preferably, the cavities 865 are substantially circular. When torque is applied on the cover 861 that is greater than a predetermined amount, the tabs 855 push the cover 861 away from the hub 851 such that the raised ring 853 is received by the lip 864 of the cover 861. Audible indicia is generated as the tabs 855 pass over the cavities 865, thereby indicating proper attachment of the hub 851 to the pen injector.

Figure 31:
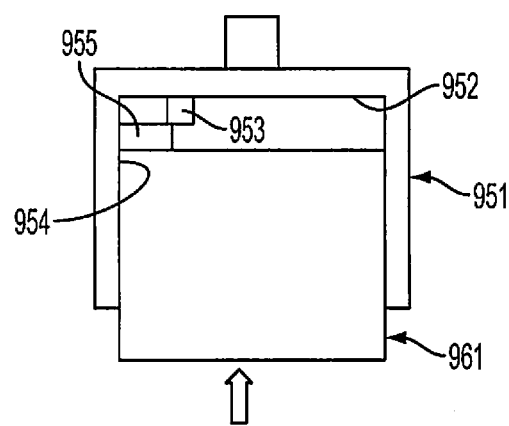
FIG. 31 is a schematic view of a pen needle hub disposed in a cover according to a ninth exemplary embodiment of the present invention.

A ninth exemplary embodiment of the present invention is shown in FIG. 31. A pen needle hub 951 has a first tab 953 and a second tab 954 disposed therein. Preferably, the first tab 951 is disposed on a first surface 952 and the second tab 955 is disposed on a second surface 954. The second tab 955 initially contacts an edge of the first tab 953, as shown in FIG. 31. When the hub 951 is threadably engaged with a pen 961 as indicated by the arrow in FIG. 31, the pen contacts the second tab 955, thereby causing the second tab 955 to pass along the first tab 953. The contact between the first and second tabs generates audible indicia to indicate proper attachment between the pen 961 and the pen needle.

Figure 32:
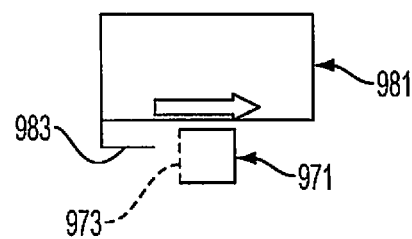
FIG. 32 is a schematic view of a pen needle hub disposed in a cover according to a tenth exemplary embodiment of the present invention.

A tenth exemplary embodiment of the present invention is shown in FIG. 32. The cover 971 has a breakable membrane 973. When a pen needle is threadably engaged with a pen, as indicated by the arrow in FIG. 32, a protrusion 983 on the hub 981 breaks the membrane 973 on the cover 971. This generates audible indicia indicating proper attachment of the pen needle to the pen.

Each of the above-described exemplary embodiments results in the generation of audible indicia indicating proper attachment of a pen needle to a pen. However, each of these exemplary embodiments also generates corresponding tactile indicia. Some environments in which the pen needle is used may be noisy such that the user cannot hear the generated audible indicia, or the user may be hearing impaired. Thus, the tactile indicia provide an alternate indication that proper attachment of the pen needle to the pen. The tactile indicia may include a user sensing a wave of a torque of peak value followed by a torque of lesser value.

The foregoing embodiments and advantages are merely exemplary and are not to be construed as limiting the scope of the present invention. The description of an exemplary embodiment of the present invention is intended to be illustrative, and not to limit the scope of the present invention. Various modifications, alternatives and variations will be apparent to those of ordinary skill in the art, and are intended to fall within the scope of the invention, as defined in the appended claims.

What is claimed is:
1. A hub assembly for an injection apparatus, comprising:
a cover;
a hub disposed in said cover and having first and second ends and outer and inner surfaces, an opening being formed at said first end and threads being formed on said inner surface proximal said second end to facilitate connecting said hub assembly to a cartridge of said injection apparatus; and
a ring disposed inside said hub, said ring having a central opening to receive a cannula, an outer edge with at least one flexible tab engaging said threads, said ring being in a first position spaced from said second end, said ring having a flat configuration with a planar first side configured for contacting an inner face of said needle hub when said cartridge is coupled to said hub, and a planar outer face configured for contacting the cartridge of the injection apparatus when coupling the hub assembly to the cartridge, and where said ring has an outer annular surface extending between said first side and second side, and where said at least one tab extends outwardly from said outer annular surface;
wherein rotation of said cover and hub with respect to the cartridge causes said ring to move with respect to said threads toward said first end to a second position where said at least one flexible tab slides over said threads in a linear direction toward said first end of said hub to create audible indicia with said threads to indicated said hub is seated on said cartridge.
2. The hub assembly for an injection apparatus according to claim 1, wherein said at least one flexible tab of said ring comprises a first tab and a second tab extending from opposite sides of said ring and engage said threads, and where said first tab and second tab create said audible indicia with said threads.

3. The hub assembly for an injection apparatus according to claim 2, wherein said first tab and said second tab slide over said threads to create the audible indicia.

4. The hub assembly of claim 1, wherein said hub has an inner axial surface facing said opening and a post extending from said inner axial surface in a direction toward said opening for supporting a cannula, and wherein said central opening in said ring has an inner dimension to receive said post when said ring seats against said inner axial surface.

5. The needle hub of claim 1, wherein
said at least one tab comprises two flexible tabs extending outwardly from said outer annular surface and engaging said threads on said hub.

* * * * *